(12) United States Patent
Liu et al.

(10) Patent No.: US 10,646,454 B2
(45) Date of Patent: *May 12, 2020

(54) MICROCELL DELIVERY SYSTEMS INCLUDING CHARGED OR MAGNETIC PARTICLES FOR REGULATING RATE OF ADMINISTRATION OF ACTIVES

(71) Applicant: E INK CALIFORNIA, LLC, Fremont, CA (US)

(72) Inventors: Lei Liu, Fremont, CA (US); Lin Shao, Fremont, CA (US); Chung Hui Lee Liu, Fremont, CA (US); Hui Du, Milpitas, CA (US); Ming Wang, Fremont, CA (US)

(73) Assignee: E INK CALIFORNIA, LLC, Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/933,463

(22) Filed: Mar. 23, 2018

(65) Prior Publication Data

US 2018/0271799 A1    Sep. 27, 2018

Related U.S. Application Data

(60) Provisional application No. 62/585,681, filed on Nov. 14, 2017, provisional application No. 62/475,929, filed on Mar. 24, 2017.

(51) Int. Cl.
*A61K 9/70* (2006.01)
*A61K 47/10* (2017.01)
(Continued)

(52) U.S. Cl.
CPC .......... *A61K 9/7084* (2013.01); *A61K 9/0009* (2013.01); *A61K 9/7092* (2013.01);
(Continued)

(58) Field of Classification Search
CPC .... A61K 9/0009; A61K 9/7092; A61K 47/10; A61K 47/32; A61K 47/14; A61K 9/7084
See application file for complete search history.

(56) References Cited

U.S. PATENT DOCUMENTS 4,559,222 A    12/1985    Enscore
4,640,689 A    2/1987    Sibalis
(Continued)

FOREIGN PATENT DOCUMENTS

EP    1457233 A1    9/2004
KR    19980025307 A    7/1998

OTHER PUBLICATIONS

Xuan et al., "Synthesis of Fe3O4 Polyaniline core shell Microsphere with well-defined Blackberry-like Morphology", J. Phy. Chem. C, 2008, 112, 18804-18809. (Year: 2008).*

(Continued)

*Primary Examiner* — Jianfeng Song
(74) *Attorney, Agent, or Firm* — Ioannis Constantinides

(57) ABSTRACT

An active molecule delivery system whereby active molecules can be released on demand and/or a variety of different active molecules can be delivered from the same system and/or different concentrations of active molecules can be delivered from the same system. The active delivery system includes a plurality of microcells, wherein the microcells are filled with a medium including an active ingredient and charged or magnetic particles. The microcells include an opening, and the opening is spanned by a porous diffusion layer. Because the porous diffusion layer can be blocked with the charged or magnetic particles, the rate at which the active ingredient is dispensed can be controlled with an electric or magnetic field, respectively.

16 Claims, 10 Drawing Sheets

(51) Int. Cl.
*A61K 47/14* (2017.01)
*A61K 47/32* (2006.01)
*A61K 9/00* (2006.01)

(52) U.S. Cl.
CPC .............. *A61K 47/10* (2013.01); *A61K 47/14* (2013.01); *A61K 47/32* (2013.01)

(56) References Cited

U.S. PATENT DOCUMENTS

| | | | |
|---|---|---|---|
| 4,734,090 A | 3/1988 | Sibalis | |
| 5,125,894 A | 6/1992 | Phipps | |
| 5,135,479 A | 8/1992 | Sibalis | |
| 5,486,362 A * | 1/1996 | Kitchell | A61K 9/1647 |
| | | | 424/423 |
| 5,533,995 A | 7/1996 | Corish | |
| 5,591,767 A | 1/1997 | Mohr | |
| 5,603,693 A | 2/1997 | Frenkel | |
| 5,797,898 A | 8/1998 | Santini, Jr. | |
| 5,931,804 A | 8/1999 | Sibalis | |
| 5,980,943 A | 11/1999 | Ayer | |
| 6,521,191 B1 | 2/2003 | Schenk | |
| 6,564,093 B1 | 5/2003 | Ostrow | |
| 6,757,560 B1 | 6/2004 | Fischer | |
| 6,933,098 B2 | 8/2005 | Chan-Park | |
| 6,980,855 B2 | 12/2005 | Cho | |
| 7,229,556 B1 | 6/2007 | Hinds, III | |
| 7,315,758 B2 | 1/2008 | Kwiatkowski | |
| 7,383,083 B2 | 6/2008 | Fischer | |
| 7,537,590 B2 | 5/2009 | Santini, Jr. | |
| 7,604,628 B2 | 10/2009 | Santini, Jr. | |
| 7,611,481 B2 | 11/2009 | Cleary | |
| 7,715,088 B2 | 5/2010 | Liang | |
| 7,892,221 B2 | 2/2011 | Santini, Jr. | |
| 8,095,213 B1 | 1/2012 | Sexton | |
| 8,257,324 B2 | 9/2012 | Prausnitz | |
| 8,403,915 B2 | 3/2013 | Santini, Jr. | |
| 8,440,222 B2 | 5/2013 | Hausner | |
| 8,517,958 B2 | 8/2013 | Eppstein | |
| 8,696,637 B2 | 4/2014 | Ross | |
| 8,744,569 B2 | 6/2014 | Imran | |
| 8,830,561 B2 | 9/2014 | Zang | |
| 8,862,223 B2 | 10/2014 | Yanaki | |
| 8,962,014 B2 | 2/2015 | Prinz | |
| 8,968,699 B2 | 3/2015 | Jin | |
| 9,188,829 B2 | 11/2015 | Li | |
| 9,327,105 B2 | 5/2016 | Ramdas | |
| 9,388,307 B2 | 7/2016 | Li | |
| 2005/0191337 A1 * | 9/2005 | Gueret | A61K 8/0208 |
| | | | 424/448 |
| 2006/0009731 A1 | 1/2006 | Wu | |
| 2007/0196456 A1 | 8/2007 | Stevens | |
| 2007/0248657 A1 | 10/2007 | Smith | |
| 2007/0292463 A1 | 12/2007 | Spector | |
| 2009/0234214 A1 | 9/2009 | Santini, Jr. | |
| 2010/0189793 A1 | 7/2010 | Meyer | |
| 2011/0046557 A1 | 2/2011 | Lee | |
| 2011/0111013 A1 | 5/2011 | Salman | |
| 2011/0196474 A1 * | 8/2011 | Davalian | A61K 9/0009 |
| | | | 623/1.15 |
| 2012/0176663 A1 * | 7/2012 | Zang | C09K 19/544 |
| | | | 359/296 |
| 2013/0096486 A1 | 4/2013 | Schroeder | |
| 2013/0289516 A1 | 10/2013 | Kosel | |
| 2014/0330223 A1 | 11/2014 | Schurad | |
| 2014/0364794 A1 | 12/2014 | Jordan | |
| 2015/0301425 A1 | 10/2015 | Du | |
| 2016/0045158 A1 | 2/2016 | Hsu | |
| 2016/0279072 A1 | 9/2016 | Li | |
| 2017/0121563 A1 | 5/2017 | Moran | |
| 2017/0205649 A1 | 7/2017 | Wang | |
| 2018/0271800 A1 | 9/2018 | Liu | |

OTHER PUBLICATIONS

Korean Intellectual Property Office, PCT/US2018/023917, International Search Report and Written Opinion, dated Jul. 10, 2017.
Korean Intellectual Property Office, PCT/US2018/023928, International Search Report and Written Opinion, dated Jul. 10, 2018.
Korean Intellectual Property Office, PCT/US2018/023921, International Search Report and Written Opinion, dated Jul. 10, 2018.
Kaiyong Cai et al., "Magnetically triggered reversible Controlled Drug Delivery from Microfabricated Polymeric Multireservior Devices"., Advanced Materials. 2009, 21, 4045-4049.
Ebbert et al., "Drugs", 70(6), pp. 643-650, 2010.
Harvey, T.G.; "Replication techniques for micro-optics"; SPIE Proc. vol. 3099, pp. 76-82; 1997.
Korean Intellectual Property Office, PCT/US2018/060259, International Search Report and Written Opinion, dated Apr. 29, 2019. Apr. 29, 2019.
Korean Intellectual Property Office, PCT/US2018/060266, International Search Report and Written Opinion, dated Apr. 29, 2019. Apr. 29, 2019.
Sahoo et al., "A Review of Transdermal drug delivery system", Journal der Pharmazie Forschung, vol. 2, N-1, 2013, 32-56 (2013) 2013.
Huang, W. C. et al.., "A flexible drug delivery chip for the magnetically-controlled release of anti-epileptic drugs", Journal of Controlled Release, vol. 139, Issue 3, Nov. 3, 2009, pp. 221-228 Nov. 3, 2009.

* cited by examiner

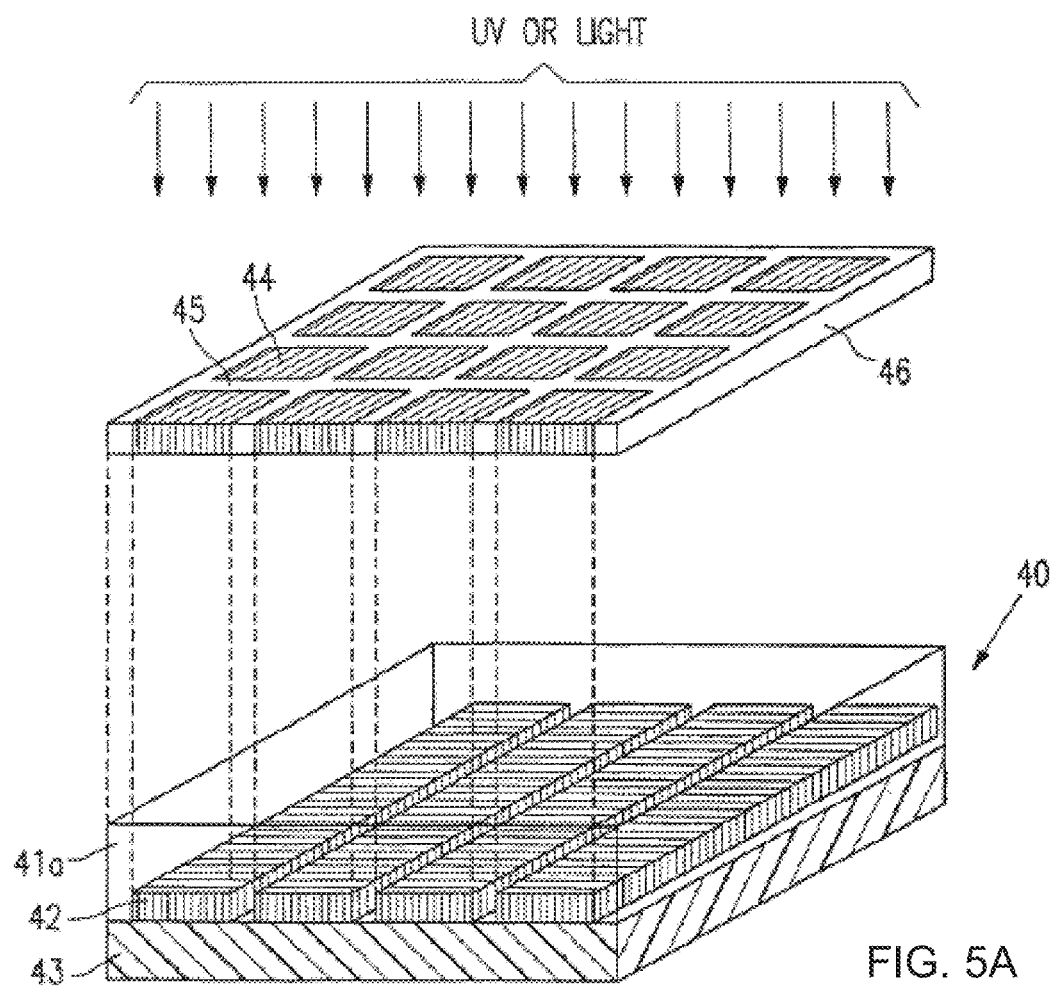
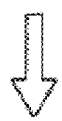
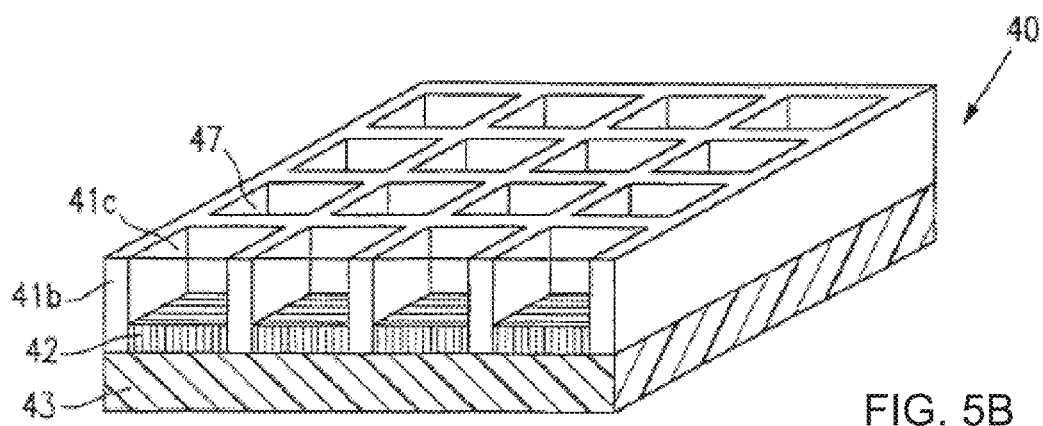
FIG. 5A
FIG. 5B

MICROCELL DELIVERY SYSTEMS INCLUDING CHARGED OR MAGNETIC PARTICLES FOR REGULATING RATE OF ADMINISTRATION OF ACTIVES

RELATED APPLICATIONS

This application claims priority to U.S. Provisional Application No. 62/475,929, filed Mar. 24, 2017, and U.S. Provisional Application No. 62/585,681, filed Nov. 14, 2017, both of which are incorporated herein in their entireties.

BACKGROUND

Transdermal delivery of pharmaceutical agents has proven effective for drugs that are able to move across the skin barrier. For example, small amounts of nicotine can be delivered over extended periods with transdermal patches that suspend the nicotine in an ethylene vinyl acetate (EVA) copolymer. See, e.g., Nicoderm-CQ® by GlaxoSmithKline (Brentford, UK). However, it is not possible to actively control the rate of administration. Rather, a series of different concentrations of nicotine suspended in EVA are provided to a user with instructions to use different patches on different days depending upon the treatment program or the level of craving.

It is recognized that the constant dosage delivered by a passive matrix of active agents may not be optimal for treating all conditions, however. For example, with respect to smoking cessation, it is recognized that the average smoker has cyclical cravings corresponding with normal daily activity, such as a waking, meals, etc. Accordingly, for some patients it is better to use a "dual therapy" including a transdermal patch and a fast acting delivery method, such as nicotine gum. See, Ebbert et al., *Drugs* 2010, 70(6), 643-650. Such dosing helps to wean the body from the dependency while also being responsive to the cyclical peak cravings. Other transdermally-delivered actives, such as insulin, also require "boosters" to overcome daily metabolic swings, e.g., following meals.

New "smart" transdermal patches that provide some ability to control dosing in real time, are currently being evaluated. For instance, Chrono Therapeutics (Hayward, Calif.) is currently testing a micropump-enabled smart transdermal patch for delivering nicotine. Chrono's device includes a "crave" button that allows users to receive a "booster" when cravings strike. Nonetheless, the Chrono device is larger than a typical transdermal patch and, thus, is visible through clothing as a sizeable bump. It also requires replacement cartridges and charging to maintain function. It is clear that there remains a need for a simple (and inexpensive) delivery system that provides for real-time modification of dosing.

SUMMARY

The invention addresses this need by providing a low power transdermal delivery system whereby the active molecules can be released on demand. Additionally, as described below, the invention provides a system for delivering varying concentrations of active molecules from the same delivery system at different times, and for delivering multiple drugs at the same, or different, times from the same patch.

Thus, in one aspect the invention is an active molecule delivery system including a plurality of microcells. The microcells may be square, round, or polygonal, such as a honeycomb structure. Each microcell includes an opening that is spanned by a porous diffusion layer. The porous diffusion layer may be constructed from a variety of materials, such acrylate, methacrylate, polycarbonate, polyvinyl alcohol, cellulose, poly(N-isopropylacrylamide) (PNIPAAm), poly(lactic-co-glycolic acid) (PLGA), polyvinylidene chloride, acrylonitrile, amorphous nylon, oriented polyester, terephthalate, polyvinyl chloride, polyethylene, polypropylene, or polystyrene. Typically, each microcell has a volume greater than 100 nL, and the porous diffusion layer has an average pore size of between 1 nm and 100 nm.

The microcells can be filled with a variety of materials. In an embodiment, microcells may be filled with a mixture of an active molecule and charged particles, and the system includes a source of an electric field. In another embodiment, microcells may be filled with a mixture of an active molecule and magnetic particles, and the system includes a source of a magnetic field. In other embodiments the system may include both charged particles and magnetic particles and the system include both a source of an electric field and a source of a magnetic field. The charged particles may comprise a charged core particle and a polymer layer surrounding the core particle, while the magnetic particles may comprise a magnetic core particle and a polymer layer surrounding the core particle. In some embodiments, the mixture further includes a plurality of charge control agents.

In both charged particle and magnetic particle embodiments, charged (magnetic) particles limit diffusion of active molecules across the porous diffusion layer when the charged (magnetic) particles are adjacent to the porous diffusion layer. This condition is achieved with a suitable electric or magnetic field, provided by the source, which causes the charged (magnetic) particles to block the pores of the diffusion layer. In some embodiments, the source of an electric field is first and second electrodes, whereby the mixture of an active molecule and charged particles is sandwiched between the first and second electrodes. For example, the first electrode or the second electrode could be part of an active matrix of electrodes. This active matrix may allow the delivery rate of individual microcells to be controlled. In some embodiments, the first electrode or the second electrode is porous, for example a porous film coated with a conductor such as indium tin oxide (ITO). Alternatively, the first or the second electrode may include a matrix of nanotubes that are both conductive and porous to the active molecules to be delivered.

In other embodiments, the microcells includes a mixture of an active molecule and magnetic particles, wherein the magnetic particles are movable within the microcell with a source of a magnetic field. In an embodiment, the magnetic particles comprise a magnetic core particle and a polymer layer surrounding the core particle. Similar to the charged particles discussed above, the magnetic particles limit diffusion of the active molecule across the porous diffusion layer when the magnetic particles are adjacent to the porous diffusion layer. The source of a magnetic field may be an electromagnet, and in some embodiments the system will include a matrix of electromagnets, wherein individual electromagnets in the matrix are addressable to allow for activation of groups of microcells or individual microcells.

In some embodiments, the mixture of an active molecule and charged particles or the mixture of an active molecule and magnetic particles are distributed in a biocompatible non-polar liquid, such as an oil, such as vegetable, fruit, or nut oil. In other embodiments, the mixture of an active molecule and charged particles or the mixture of an active molecule and magnetic particles are distributed in an aqueous liquid, such as water or a buffer. The mixtures may also include charge control agents, surfactants, nutrients, and adjuvants. Typically, the active molecule is a pharmaceutical compound, however systems of the invention can be used to deliver hormones, nutraceuticals, proteins, nucleic acids, antibodies, or vaccines. Because the invention includes a plurality of microcells, it is possible to have different microcells within the same device containing different mixtures or similar mixtures having different concentrations. For example, a system may include first microcells containing a mixture of first active molecules and second microcells containing a mixture of second active molecules, or a system may include first microcells containing active molecules at a first concentration and second microcells containing the same active molecules at a second concentration. In other embodiments, the system may include first microcells containing a mixture of active molecules and second microcells containing an adjuvant. Other combinations of active molecules, agents, and concentrations will be evident to one of skill in the art.

BRIEF DESCRIPTION OF THE DRAWINGS

In FIG. 2, the charged or magnetic particles move laterally to regulate movement of active molecules via the walls of the microcells;

FIGS. 5A and 5B detail the production of microcells for an active molecule delivery system using photolithographic exposure through a photomask of a conductor film coated with a thermoset precursor;

In FIGS. 5C and 5D a combination of top and bottom exposure is used, allowing the walls in one lateral direction to be cured by top photomask exposure, and the walls in another lateral direction to be cured bottom exposure through the opaque base conductor film. This process allows microcell walls to be prepared with varying porosity for use with lateral motion embodiments;

In FIG. 7A, the charged particles are moved by an electric field between electrodes above and below the medium including the active molecules and the charged particles;

In FIG. 7B, the charged particles are moved by an electric field between an electrode above the medium while the conductivity of the skin provides a grounding electrode;

In FIG. 7C, the magnetic particles are moved by an external magnetic field;

In FIG. 8, a switch is coupled to a wireless receiver allowing a user to alter the rate of delivery with an application on a mobile phone or other wireless device;

In FIG. 9, an active matrix of electrodes is coupled to a matrix driver that is coupled to a wireless receiver, thereby allowing an application to alter the type of active molecule that is being delivered;

DESCRIPTION

The invention provides an active molecule delivery system whereby active molecules can be released on demand and/or a variety of different active molecules can be delivered from the same system and/or different concentrations of active molecules can be delivered from the same system. The invention is well-suited for delivering pharmaceuticals to patients transdermally, however the invention may be used to deliver active ingredients to animals, generally. For example, the invention can deliver tranquilizing agents to a horse during transport. The active delivery system includes a plurality of microcells, wherein the microcells are filled with a medium including an active ingredient and charged or magnetic particles. The microcells include an opening, and the opening is spanned by a porous diffusion layer. Because the porous diffusion layer can be blocked with the charged or magnetic particles, the rate at which the active ingredient is dispensed can be controlled. Additionally, the microcell arrays may be loaded with different active ingredients, thereby providing a mechanism to deliver different or complimentary active ingredients on demand.

In addition to more conventional applications, such as transdermal delivery of pharmaceutical compounds, the active molecule delivery system may be the basis for delivering agricultural nutrients. The microcell arrays can be fabricated in large sheets that can be used in conjunction with hydroponic growing systems, or they can be integrated into hydrogel film farming, such as demonstrated by Mebiol, Inc. (Kanagawa, Japan). The active molecule delivery systems can be incorporated into the structural walls of smart packing, as well. The delivery system, for example, makes it possible to have long term release of antioxidants into a package containing fresh vegetables. Such packaging will dramatically improve the shelf life of certain foods, yet will only require the amount of antioxidant necessary to maintain freshness until the package is opened.

Figure 1:
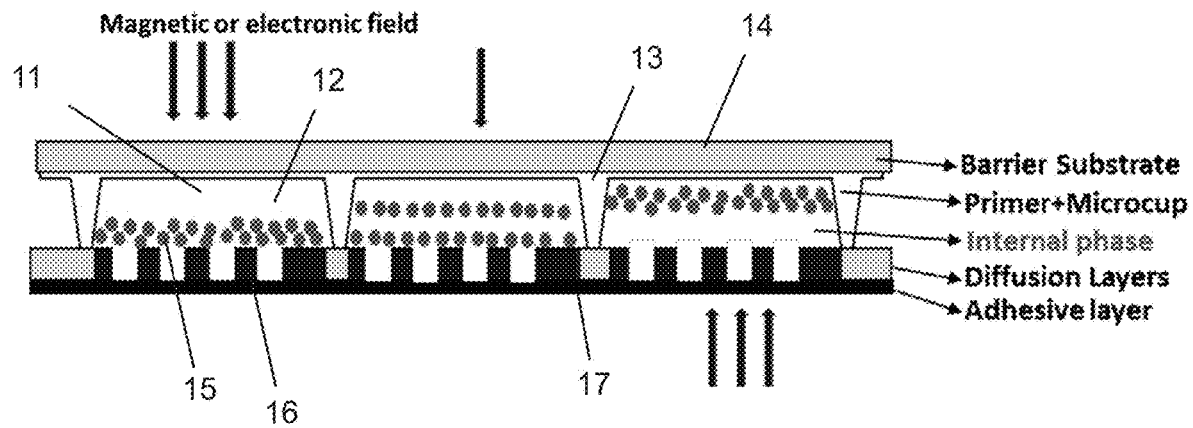
FIG. 1 illustrates an embodiment of an active molecule delivery system including a plurality of microcells and charged or magnetic particles that regulate movement of active molecules across a porous diffusion layer.

An overview of an active molecule delivery system is shown in FIG. 1. The system includes a plurality of microcells 11, each microcell including a medium 12 (a.k.a. internal phase), that includes an active molecule and a charged (or magnetic) particle 15. Each microcell 11 is part of an array that is formed from a polymer matrix 13, which is described in more detail below. The active molecule delivery system will typically include a backing barrier 14 to provide structural support and protection against moisture ingress and physical interactions. A portion of the microcell 11 will have an opening that is spanned by a porous diffusion layer 16, which may be constructed from a variety of natural or non-natural polymers, such as comprises acrylates, methacrylates, polycarbonates, polyvinyl alcohols, cellulose, poly(N-isopropylacrylamide) (PNIPAAm), poly(lactic-co-glycolic acid) (PLGA), polyvinylidene chloride, acrylonitrile, amorphous nylon, oriented polyester, terephthalate, polyvinyl chloride, polyethylene, polypropylene, or polystyrene. Often the system will additionally include an adhesive layer 17 that is also porous to the active molecule. The adhesive layer 17 assists in keeping the active molecule delivery system adjacent to the surface. As shown in FIG. 1, the particles 15 can be caused to move within the microcell 11 such that the particles 15 restrict the motion of the active molecules through the porous diffusion layer 16. In embodiments where the particles are charged, the motion of the particles can be controlled with an electric field. In embodiments where the particles are magnetic, the motion of the particles can be controlled with a magnetic field. Of course, it is possible to have both charged and magnetic particles in the same system or even in the same microcell.

The charged particles will typically comprise a charged core with a surrounding polymer layer. Methods for constructing such particles can be found, for example, in U.S. Patent Publication No. 2015/0301425, which is incorporated herein by reference in its entirety. Thus, the core particle may be an inorganic or an organic material, such as $TiO_2$, $BaSO_4$, ZnO, metal oxides, manganese ferrite black spinel, copper chromite black spinel, carbon black or zinc sulfide pigment particles. In some embodiments, the charged particles may have a surface treatment that increases the charge density on the core particle. For example, the core particle may be surface treated with an organic silane having functional groups, such as acrylate, vinyl, $—NH_2$, —NCO, —OH or the like, for example a polyacrylate, polyurethane, polyurea, polyethylene, polyester, polysiloxane or the like. For example, a polyacrylate shell may be formed from monomer, such as styrene, methyl acrylate, methyl methacrylate, n-butyl acrylate, n-butyl methacrylate, t-butyl acrylate, t-butyl methacrylate, vinyl pyridine, n-vinyl pyrrolidone, 2-hydoxyethyl acrylate, 2-hydroxyethyl methacrylate, dimethylaminoethyl methacrylate or the like. A polyurethane shell may be formed from monomer or oligomer, such as multifunctional isocyanate or thioisocyanate, primary alcohol or the like. A polyurea shell may also be formed from monomer containing reactive groups, such as amine/isocyanate, amine/thioisocyanate or the like. The charged particles are additionally covered with steric-stabilizing polymers. The steric stabilizing polymers may be covalently bound to the surface of the charged core particles or the steric stabilizers may be merely associated with the core particle. Such stabilizing molecules usually formed of high molecular weight polymers, such as polyethylene, polypropylene, polyester, polysiloxane or a mixture thereof. The steric stabilizers should be compatible with the solvent in which the composite pigment particles are dispersed to facilitate dispersion of the composite pigment particles in the solvent. Methods for preparing such charged particle are described in U.S. Patent Publication No. 2015/0301425.

Embodiments using magnetic particles will include core magnetic particles, however the core magnetic particles may be coated with steric stabilizing molecules as described above. For example magnetic particles may be $Fe_3O_4$ core particles created by dissolving $FeCl_3.6H_2O$ with sodium acetate and ethylene glycol and then adding polyethylene glycol during crystallization. The invention is not limited to ferromagnetic materials as other magnetic particles such as nickel and cobalt may be preferred for applications in which iron-based particles will interact negatively with active ingredients. Commercially-available magnetic particles of suitable size (typically about 50 nm), and of varying compositions, are available from Sigma-Aldrich (Milwaukee, Wis.).

Figure 2:
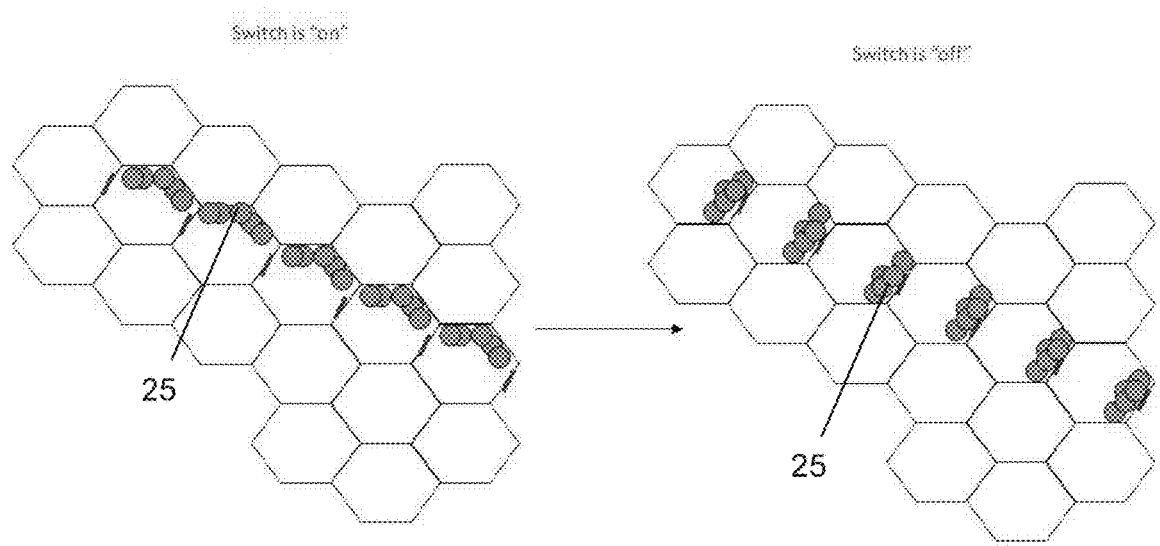
FIG. 2 illustrates an embodiment of an active molecule delivery system including a plurality of microcells and charged or magnetic particles that regulate diffusion of active molecules across a porous diffusion layer.

FIG. 2 shows an alternative construction of an active molecule delivery system. In the construction of FIG. 2, a portion of each microcell wall is sufficiently porous to pass active molecules between microcells. The rate of passage can be controlled with the movement of charged particles 25 with perimeter electrodes (not shown). In some embodiments, the electrodes for effecting movement of the particles 25 are deposited inside the microcells and connected to leads that supply the voltage. In other embodiments, the electrodes at not inside the microcells, but rather below the microcells, similar to the construction shown in FIG. 7A. Additional second order techniques, such as electro-osmosis and dielectrophoresis may be employed to position the particles to slow movement of the active molecules between microcells. While not shown in FIG. 2, it is understood that a portion of the microcells will have opening to all the active molecules to pass out of the microcells.

Figure 3A:
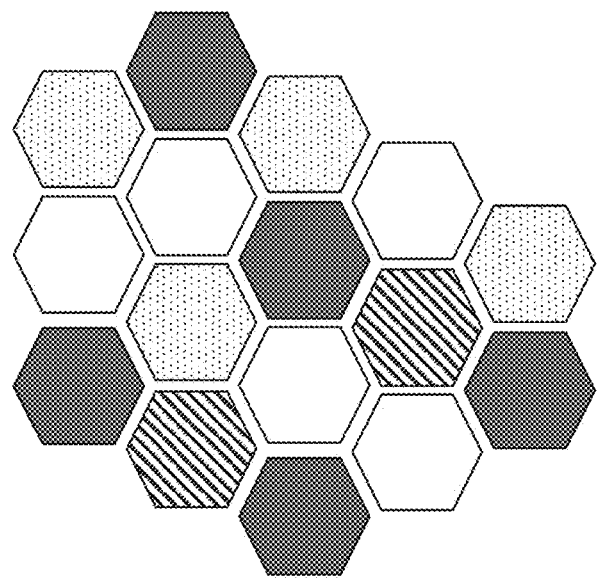
FIG. 3A illustrates an active molecule delivery system including a plurality of different types of actives and/or a plurality of concentrations of actives in the same delivery system. Because the microcells can be individually addressed with an active matrix, it is possible to provide varying actives on demand and also to produce complex dosing profiles.
Figure 3B:
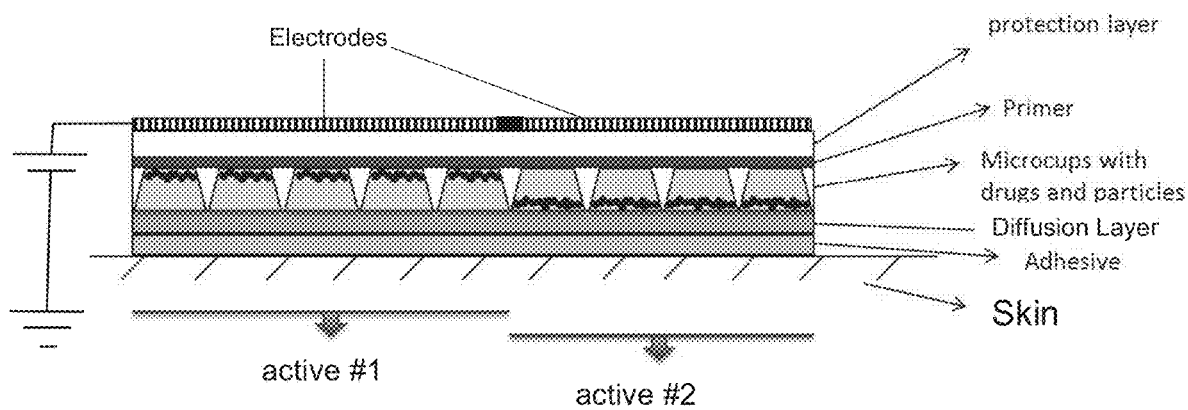
FIG. 3B illustrates an active molecule delivery system wherein some of the active molecules are released quickly while other active molecules are released at a slower rate because charged or magnetic particles are limiting movement of the active molecules across the porous diffusion layer.

In addition to regulating the flow of active molecules, the microcell construction of the invention lends itself to making arrays of differing active molecules, or arrays of different concentrations, as illustrated in FIG. 3. Using picoliter injection with inkjet or other fluidic systems, individual microcells can be filled to enable a variety of different actives to be included in an active molecule delivery system. For example, a system of the invention may include nicotine at four different concentrations, thereby allowing different dosages to be delivered at different times during the day. For example, shortly after waking the most concentrated dose may be delivered (dark gray), followed by a much lower taper dose during the day (speckled), until the time that a user needs another more concentrated dose. It is possible to also include different actives in the same microcell. For example, the system of FIGS. 3A and 3B may also include an analgesic (stripes) to reduce swelling and itching in the area of the skin that is in contact with the delivery system. Of course, a variety of combinations are possible, and varying microcells might include pharmaceuticals, nutraceuticals, adjuvants, vitamins, or vaccines. Furthermore, the arrangement of the microcells may not be distributed. Rather the microcells may be filled in clusters, which makes filling and driving more straightforward. In other embodiments, smaller microcell arrays may be filled with the same medium, i.e., having the same active molecule at the same concentration, and then the smaller arrays assembled into a larger array to make a delivery system of the invention.

As shown in FIG. 3B, this arrangement also allows for two different actives to be delivered at two different rates. A first active may be most effective dosed at a faster rate, which is achieved when there are few particles blocking passage of actives across the diffusion layer, i.e., the left side of FIG. 3B. However, a second active may be more effective when administered at a slower rate, which is achieved when there are more particles blocking passage of actives across the diffusion layer, i.e., the right side of FIG. 3B. This differential rate limiting can be achieved by activating electrodes over the portion of the microcells for which passage is to be slowed. When properly biased, the electric field between the electrode and the skin will drive the charged particles against the diffusion layer.

Techniques for Constructing Microcells.

Figure 4:
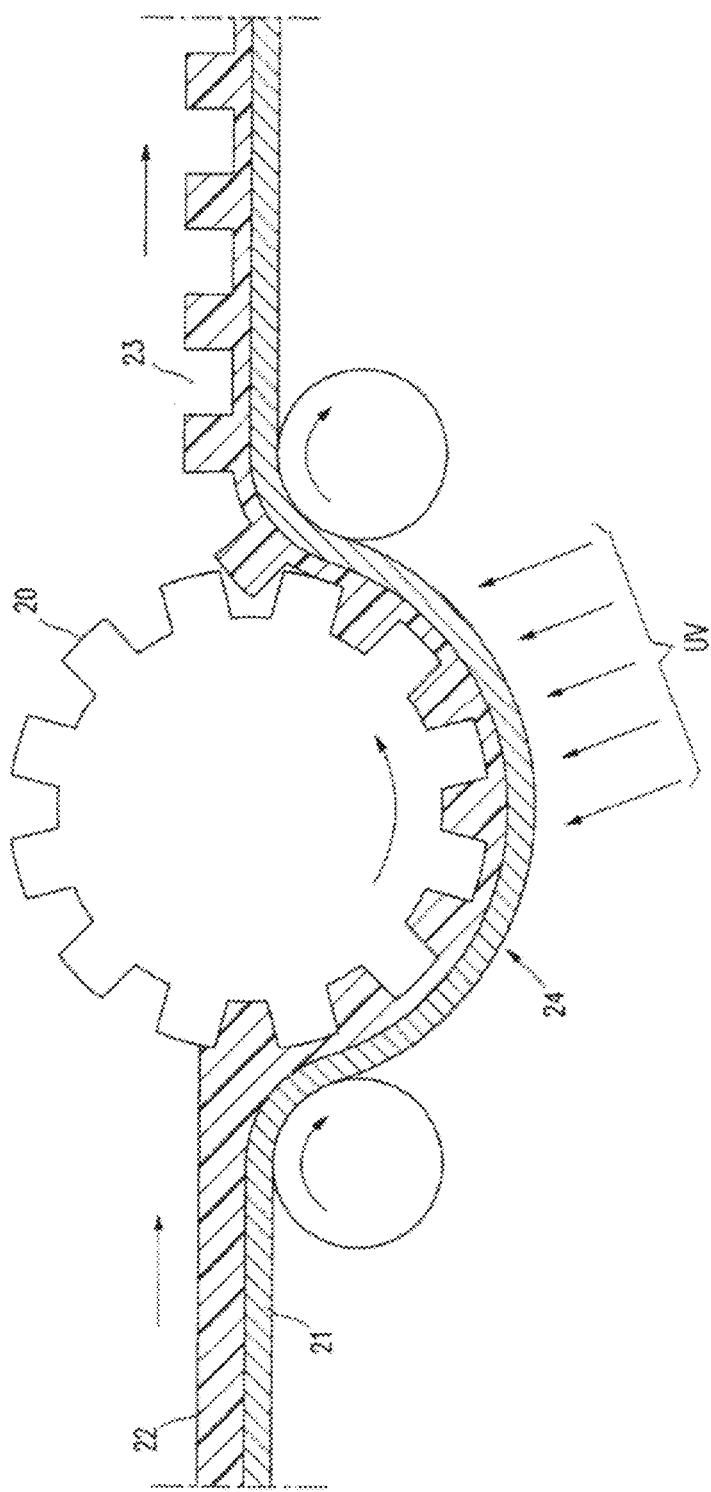
FIG. 4 shows a method for making microcells for the invention using a roll-to-roll process.

Microcells may be formed either in a batchwise process or in a continuous roll-to-roll process as disclosed in U.S. Pat. No. 6,933,098. The latter offers a continuous, low cost, high throughput manufacturing technology for production of compartments for use in a variety of applications including active molecule delivery and electrophoretic displays. Microcell arrays suitable for use with the invention can be created with microembossing, as illustrated in FIG. 4. A male mold 20 may be placed either above the web 24, as shown in FIG. 4, or below the web 24 (not shown) however alternative arrangements are possible. See U.S. Pat. No. 7,715,088, which is incorporated herein by reference in its entirety. A conductive substrate may be constructed by forming a conductor film 21 on polymer substrate that becomes the backing for a device. A composition comprising a thermoplastic, thermoset, or a precursor thereof 22 is then coated on the conductor film. The thermoplastic or thermoset precursor layer is embossed at a temperature higher than the glass transition temperature of the thermoplastics or thermoset precursor layer by the male mold in the form of a roller, plate or belt.

The thermoplastic or thermoset precursor for the preparation of the microcells may be multifunctional acrylate or methacrylate, vinyl ether, epoxide and oligomers or polymers thereof, and the like. A combination of multifunctional epoxide and multifunctional acrylate is also very useful to achieve desirable physico-mechanical properties. A cross-linkable oligomer imparting flexibility, such as urethane acrylate or polyester acrylate, may be added to improve the flexure resistance of the embossed microcells. The composition may contain polymer, oligomer, monomer and additives or only oligomer, monomer and additives. The glass transition temperatures (or $T_g$) for this class of materials usually range from about −70° C. to about 150° C., preferably from about −20° C. to about 50° C. The microembossing process is typically carried out at a temperature higher than the $T_g$. A heated male mold or a heated housing substrate against which the mold presses may be used to control the microembossing temperature and pressure.

As shown in FIG. 4, the mold is released during or after the precursor layer is hardened to reveal an array of microcells 23. The hardening of the precursor layer may be accomplished by cooling, solvent evaporation, cross-linking by radiation, heat or moisture. If the curing of the thermoset precursor is accomplished by UV radiation, UV may radiate onto the transparent conductor film from the bottom or the top of the web as shown in the two figures. Alternatively, UV lamps may be placed inside the mold. In this case, the mold must be transparent to allow the UV light to radiate through the pre-patterned male mold on to the thermoset precursor layer. A male mold may be prepared by any appropriate method, such as a diamond turn process or a photoresist process followed by either etching or electroplating. A master template for the male mold may be manufactured by any appropriate method, such as electroplating. With electroplating, a glass base is sputtered with a thin layer (typically 3000 Å) of a seed metal such as chrome inconel. The mold is then coated with a layer of photoresist and exposed to UV. A mask is placed between the UV and the layer of photoresist. The exposed areas of the photoresist become hardened. The unexposed areas are then removed by washing them with an appropriate solvent. The remaining hardened photoresist is dried and sputtered again with a thin layer of seed metal. The master is then ready for electroforming. A typical material used for electroforming is nickel cobalt. Alternatively, the master can be made of nickel by electroforming or electroless nickel deposition. The floor of the mold is typically between about 50 to 400 microns. The master can also be made using other microengineering techniques including e-beam writing, dry etching, chemical etching, laser writing or laser interference as described in "Replication techniques for micro-optics", SPIE Proc. Vol. 3099, pp. 76-82 (1997). Alternatively, the mold can be made by photomachining using plastics, ceramics or metals.

Prior to applying a UV curable resin composition, the mold may be treated with a mold release to aid in the demolding process. The UV curable resin may be degassed prior to dispensing and may optionally contain a solvent. The solvent, if present, readily evaporates. The UV curable resin is dispensed by any appropriate means such as, coating, dipping, pouring or the like, over the male mold. The dispenser may be moving or stationary. A conductor film is overlaid the UV curable resin. Pressure may be applied, if necessary, to ensure proper bonding between the resin and the plastic and to control the thickness of the floor of the microcells. The pressure may be applied using a laminating roller, vacuum molding, press device or any other like means. If the male mold is metallic and opaque, the plastic substrate is typically transparent to the actinic radiation used to cure the resin. Conversely, the male mold can be transparent and the plastic substrate can be opaque to the actinic radiation. To obtain good transfer of the molded features onto the transfer sheet, the conductor film needs to have good adhesion to the UV curable resin which should have a good release property against the mold surface.

Microcell arrays for the invention typically include a pre-formed conductor film, such as indium tin oxide (ITO) conductor lines, however other conductive materials, such as silver or aluminum may be used. The conductive material may be backed by or integrated into substrates such as polyethylene terephthalate, polyethylene naphthalate, polyaramid, polyimide, polycycloolefin, polysulfone, epoxy and their composites. The conductor film may coated with a radiation curable polymer precursor layer. The film and precursor layer are then exposed imagewise to radiation to form the microcell wall structure. Following exposure, the precursor material is removed from the unexposed areas, leaving the cured microcell walls bonded to the conductor film/support web. The imagewise exposure may be accomplished by UV or other forms of radiation through a photomask to produce an image or predetermined pattern of exposure of the radiation curable material coated on the conductor film. Although it is generally not required, the mask may be positioned and aligned with respect to the conductor film, i.e., ITO lines, so that the transparent mask portions align with the spaces between ITO lines, and the opaque mask portions align with the ITO material (intended for microcell cell floor areas).

Photolithography.

Microcells can also be produced using photolithography. Photolithographic processes for fabricating a microcell array are illustrated in FIGS. 5A and 5B. As shown in FIGS. 5A and 5B, the microcell array 40 may be prepared by exposure of a radiation curable material 41a coated by known methods onto a conductor electrode film 42 to UV light (or alternatively other forms of radiation, electron beams and the like) through a mask 46 to form walls 41b corresponding to the image projected through the mask 46. The base conductor film 42 is preferably mounted on a supportive substrate base web 43, which may comprise a plastic material.

In the photomask 46 in FIG. 5A, the dark squares 44 represent the opaque area and the space between the dark squares represents the transparent area 45 of the mask 46. The UV radiates through the transparent area 45 onto the radiation curable material 41a. The exposure is preferably performed directly onto the radiation curable material 41a, i.e., the UV does not pass through the substrate 43 or base conductor 42 (top exposure). For this reason, neither the substrate 43, nor the conductor 42, needs to be transparent to the UV or other radiation wavelengths employed.

As shown in FIG. 5B, the exposed areas 41b become hardened and the unexposed areas (protected by the opaque area 44 of the mask 46) are then removed by an appropriate solvent or developer to form the microcells 47. The solvent or developer is selected from those commonly used for dissolving or reducing the viscosity of radiation curable materials such as methylethylketone (MEK), toluene, acetone, isopropanol or the like. The preparation of the microcells may be similarly accomplished by placing a photomask underneath the conductor film/substrate support web and in this case the UV light radiates through the photomask from the bottom and the substrate needs to be transparent to radiation.

Imagewise Exposure.

Figure 5D:
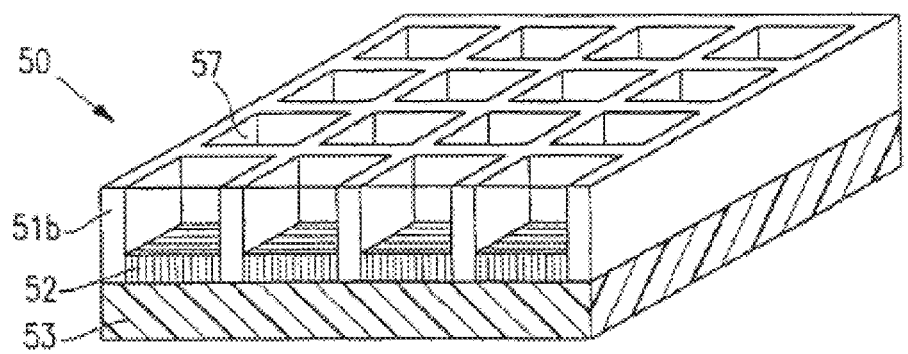
FIGS. 5C and 5D detail an alternate embodiment in which microcells for an active molecule delivery system are fabricated using photolithography.
Figure 5C:
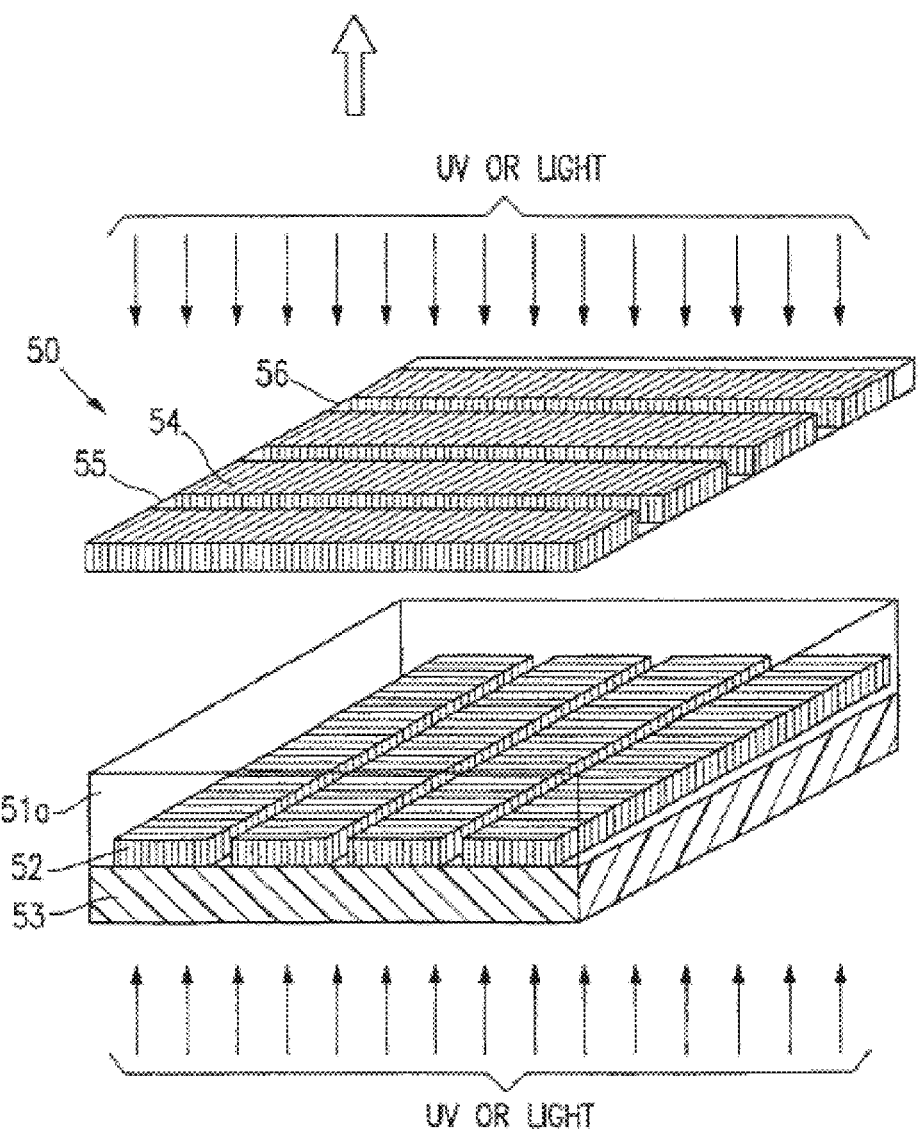

Still another alternative method for the preparation of the microcell array of the invention by imagewise exposure is illustrated in FIGS. 5C and 5D. When opaque conductor lines are used, the conductor lines can be used as the photomask for the exposure from the bottom. Durable microcell walls are formed by additional exposure from the top through a second photomask having opaque lines perpendicular to the conductor lines. FIG. 5C illustrates the use of both the top and bottom exposure principles to produce the microcell array 50 of the invention. The base conductor film 52 is opaque and line-patterned. The radiation curable material 51a, which is coated on the base conductor 52 and substrate 53, is exposed from the bottom through the conductor line pattern 52 which serves as the first photomask. A second exposure is performed from the "top" side through the second photomask 56 having a line pattern perpendicular to the conductor lines 52. The spaces 55 between the lines 54 are substantially transparent to the UV light. In this process, the wall material 51b is cured from the bottom up in one lateral orientation, and cured from the top down in the perpendicular direction, joining to form an integral microcell 57. As shown in FIG. 5D, the unexposed area is then removed by a solvent or developer as described above to reveal the microcells 57. The technique described in FIGS. 5C and 5D thus allow the different walls to be constructed with different porosity, as needed for the embodiment illustrated in FIG. 2.

The microcells may be constructed from thermoplastic elastomers, which have good compatibility with the microcells and do not interact with the electrophoretic media. Examples of useful thermoplastic elastomers include ABA, and (AB)n type of di-block, tri-block, and multi-block copolymers wherein A is styrene, α-methylstyrene, ethylene, propylene or norbonene; B is butadiene, isoprene, ethylene, propylene, butylene, dimethylsiloxane or propylene sulfide; and A and B cannot be the same in the formula. The number, n, is ≥1, preferably 1-10. Particularly useful are di-block or tri-block copolymers of styrene or ox-methylstyrene such as SB (poly(styrene-b-butadiene)), SBS (poly(styrene-b-butadiene-b-styrene)), SIS (poly(styrene-b-isoprene-b-styrene)), SEBS (poly(styrene-b-ethylene/butylenes-b-stylene)) poly(styrene-b-dimethylsiloxane-b-styrene), poly((α-methylstyrene-b-isoprene), poly(α-methylstyrene-b-isoprene-b-α-methylstyrene), poly(α-methylstyrene-b-propylene sulfide-b-α-methylstyrene), poly(α-methylstyrene-b-dimethylsiloxane-b-α-methylstyrene). Commercially available styrene block copolymers such as Kraton D and G series (from Kraton Polymer, Houston, Tex.) are particularly useful. Crystalline rubbers such as poly(ethylene-co-propylene-co-5-methylene-2-norbornene) or EPDM (ethylene-propylene-diene terpolymer) rubbers such as Vistalon 6505 (from Exxon Mobil, Houston, Tex.) and their grafted copolymers have also been found very useful.

The thermoplastic elastomers may be dissolved in a solvent or solvent mixture which is immiscible with the display fluid in the microcells and exhibits a specific gravity less than that of the display fluid. Low surface tension solvents are preferred for the overcoating composition because of their better wetting properties over the microcell walls and the electrophoretic fluid. Solvents or solvent mixtures having a surface tension lower than 35 dyne/cm are preferred. A surface tension of lower than 30 dyne/cm is more preferred. Suitable solvents include alkanes (preferably $C_{6-12}$ alkanes such as heptane, octane or Isopar solvents from Exxon Chemical Company, nonane, decane and their isomers), cycloalkanes (preferably $C_{6-12}$ cycloalkanes such as cyclohexane and decalin and the like), alkylbezenes (preferably mono- or di-$C_{1-6}$ alkyl benzenes such as toluene, xylene and the like), alkyl esters (preferably $C_{2-5}$ alkyl esters such as ethyl acetate, isobutyl acetate and the like) and $C_{3-5}$ alkyl alcohols (such as isopropanol and the like and their isomers). Mixtures of alkylbenzene and alkane are particularly useful.

In addition to polymer additives, the polymer mixtures may also include wetting agents (surfactants). Wetting agents (such as the FC surfactants from 3M Company, Zonyl fluorosurfactants from DuPont, fluoroacrylates, fluoromethacrylates, fluoro-substituted long chain alcohols, perfluoro-substituted long chain carboxylic acids and their derivatives, and Silwet silicone surfactants from OSi, Greenwich, Conn.) may also be included in the composition to improve the adhesion of the sealant to the microcells and provide a more flexible coating process. Other ingredients including cross-linking agents (e.g., bisazides such as 4,4'-diazidodiphenylmethane and 2,6-di-(4'-azidobenzal)-4-methylcyclohexanone), vulcanizers (e.g., 2-benzothiazolyl disulfide and tetramethylthiuram disulfide), multifunctional monomers or oligomers (e.g., hexanediol, diacrylates, trimethylolpropane, triacrylate, divinylbenzene, diallylphthalene), thermal initiators (e.g., dilauroryl peroxide, benzoyl peroxide) and photoinitiators (e.g., isopropyl thioxanthone (ITX), Irgacure 651 and Irgacure 369 from Ciba-Geigy) are also highly useful to enhance the physico-mechanical properties of the sealing layer by crosslinking or polymerization reactions during or after the overcoating process.

After the microcells are produced, they are filled with appropriate mixtures of active molecules and charged or magnetic particles. The microcell array 60 may be prepared by any of the methods described above. As shown in cross-section in FIGS. 6A-6D, the microcell walls 61 extend upward from the substrate 63 to form the open cells. In an embodiment using charged particles, an electrode 62 is formed on or at the substrate 63. While FIGS. 6A-6D show the electrode 62 interrupted by the microcell walls 61, it is also possible that the electrode 62 is continuous and running above, below, or within, the substrate 63. Prior to filling, the microcell array 60 may be cleaned and sterilized to assure that the active molecules are not compromised prior to use. In other embodiments, no electrode 62 is included in the construction, and an active matrix of electrodes, e.g., coupled to a display driver, is coupled to the microcell array 60 to allow individual microcells to be addressed.

Figure 6A:
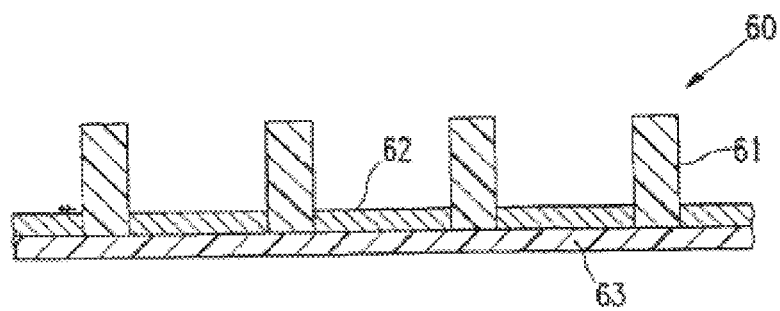
FIGS. 6A-6D illustrate the steps of filling and sealing an array of microcells to be used in an active molecule delivery system.
Figure 6B:
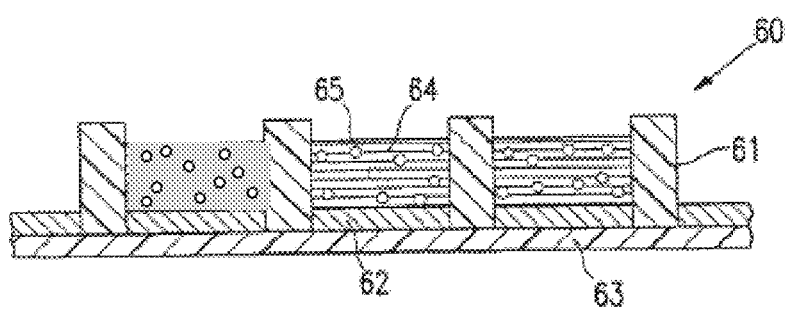

The microcells are next filled with a mixture 64 including charged or magnetic particles 65. As shown in FIG. 6B, different microcells may include different active molecules. In other embodiments (shown in FIGS. 7A-7C) the different microcells may include differing types of charged particles or the different microcells may include magnetic particles. The microcells 60 are preferably partially filled to prevent overflow and the unintentional mixing of active ingredients. In systems for delivering hydrophobic active molecules, the mixture may be based upon a biocompatible oil or some other biocompatible hydrophobic carrier. For example, the mixture may comprise a vegetable, fruit, or nut oil. In other embodiments, silicone oils may be used. In systems for delivering hydrophilic active molecules, the mixture may be based upon water or another aqueous medium such as phosphate buffer. The mixture need not be a liquid, however, as hydrogels and other matrices may be suitable to deliver the active ingredients provided that the structure of the matrix does not restrict motion of the charged or magnetic particles to the point that they cannot move to the porous diffusion layer to limit the delivery of the active molecules.

The microcells may be filled using a variety of techniques. In some embodiments, where a large number of neighboring microcells are to be filled with an identical mixture, blade coating may be used to fill the microcells to the depth of the microcell walls 61. In other embodiments, where a variety of different mixtures are to be filled in a variety of nearby microcell, inkjet-type microinjection can be used to fill the microcells. In yet other embodiments, microneedle arrays may be used to fill an array of microcells with the correct mixtures. The filling may be done in a one-step or multistep process. For example, all of the cells may be partially filled with an amount of solvent and as well as charged or magnetic particles. The partially filled microcells are then filled with a second mixture including the solvent and one or more active molecules to be delivered.

Figure 6C:
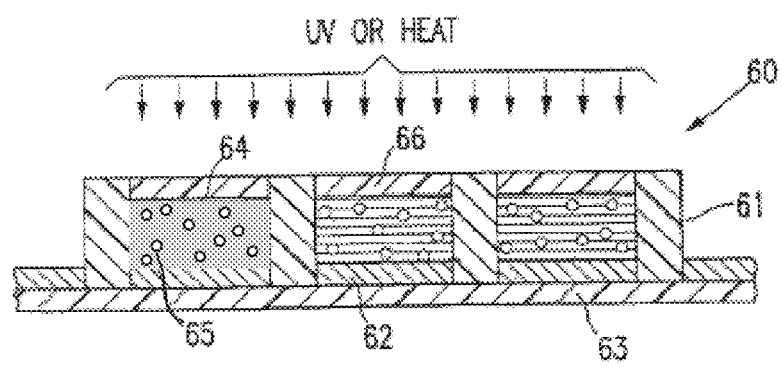
Figure 6D:
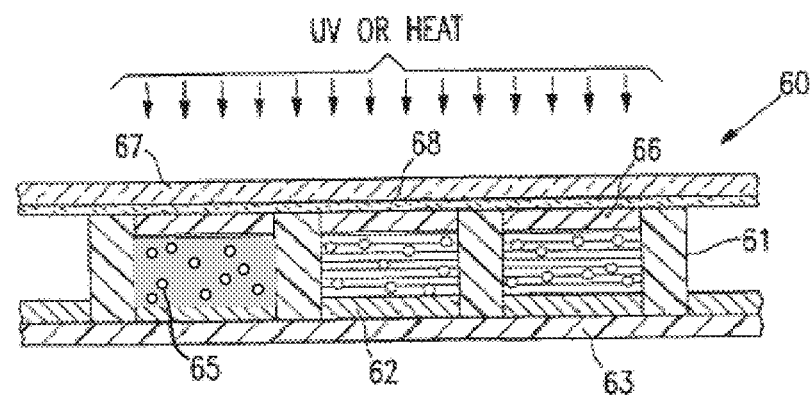

As shown in FIG. 6C, after filling, the microcells are sealed by applying a polymer 66 that becomes the porous diffusion layer. In some embodiments, the sealing process may involve exposure to heat, dry hot air, or UV radiation. In most embodiments the polymer 66 will be compatible with the mixture 64, but not dissolved by the solvent of the mixture 64. The polymer 66 will also be biocompatible and selected to adhere to the sides or tops of the microcell walls 61. A suitable biocompatible adhesive for the porous diffusion layer is a phenethylamine mixture, such as described in U.S. patent application Ser. No. 15/336,841, filed Oct. 30, 2016 and titled "Method for Sealing Microcell Containers with Phenethylamine Mixtures," which is incorporated herein by reference in its entirety. Accordingly, the final microcell structure is mostly impervious to leaks and able to withstand flexing without delamination of the porous diffusion layer.

In alternate embodiments, a variety of individual microcells may be filled with the desired mixture by using iterative photolithography. The process typically includes coating an array of empty microcells with a layer of positively working photoresist, selectively opening a certain number of the microcells by imagewise exposing the positive photoresist, followed by developing the photoresist, filling the opened microcells with the desired mixture, and sealing the filled microcells by a sealing process. These steps may be repeated to create sealed microcells filled with other mixtures. This procedure allows for the formation of large sheets of microcells having the desired ratio of mixtures or concentrations.

After the microcells 60 are filled, the sealed array may be laminated with a second conductive film 68 that is also porous to the active molecules, preferably by pre-coating the conductive film 68 with an adhesive layer which may be a pressure sensitive adhesive, a hot melt adhesive, or a heat, moisture, or radiation curable adhesive. The laminate adhesive may be post-cured by radiation such as UV through the top conductor film if the latter is transparent to the radiation. In other embodiments, an active matrix of electrodes may be bonded directly to the sealed array of electrophoretic microcell cells. In some embodiments, a biocompatible adhesive 67 is then laminated to the assembly. The biocompatible adhesive 67 will allow active molecules to pass through while keeping the device mobile on a user. Suitable biocompatible adhesives are available from 3M (Minneapolis, Minn.).

Figure 7A:
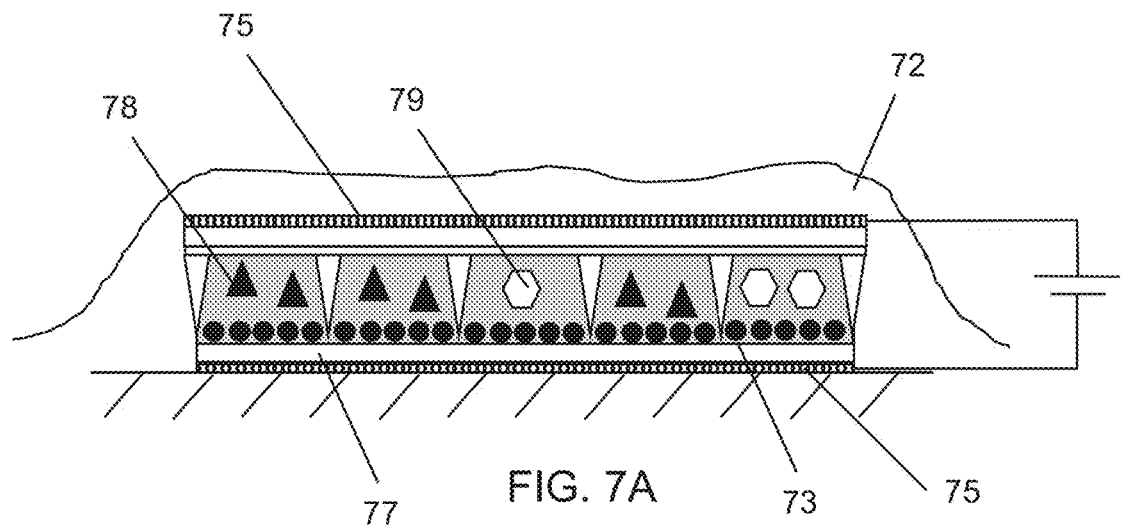
FIG. 7A illustrates an embodiment of an active molecule delivery system including a plurality of microcells and charged particles to regulate motion of active ingredients across a porous diffusion layer.
Figure 7B:
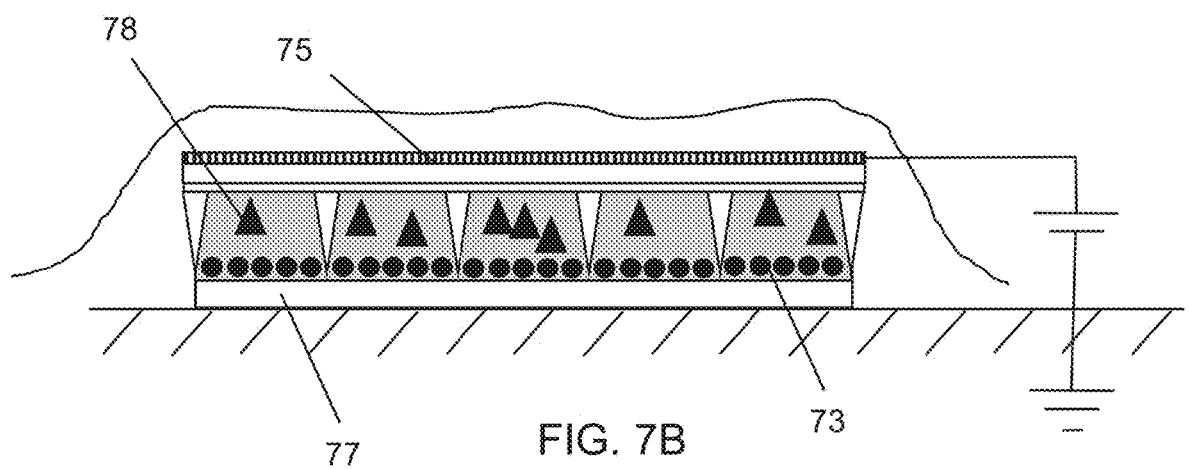
FIG. 7B illustrates an embodiment of an active molecule delivery system including a plurality of microcells and charged particles to regulate motion of active ingredients across a porous diffusion layer.
Figure 7C:
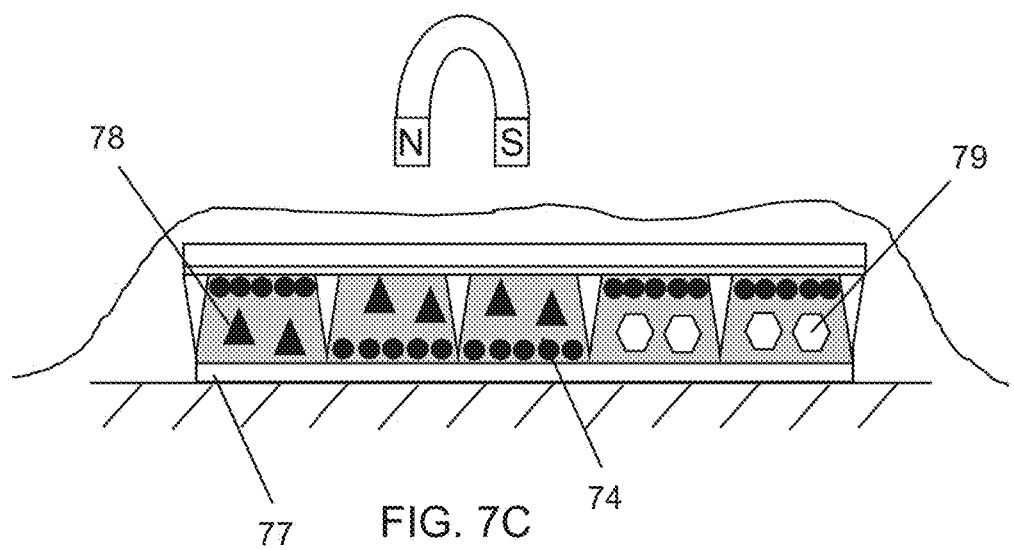
FIG. 7C illustrates an embodiment of an active molecule delivery system including a plurality of microcells and magnetic particles to regulate motion of active ingredients across a porous diffusion layer.

Once the delivery system has been constructed, it will be covered with a backing layer 72 to provide protection against physical shock. Such a backing layer 72 is shown in FIGS. 7A-7C however the thickness of the backing layer has been exaggerated for clarity. The backing layer may also include adhesives to make sure that the active molecule delivery system stays affixed, e.g., to a patient's back. The backing layer 72 may also include aesthetic coloring or fun designs for children.

FIGS. 7A-7C illustrate different modes of manipulating charged 73 or magnetic 74 particles. As shown in FIG. 7A, a delivery system using charged particle 73 may include multiple electrodes 75 to provide an electric field for driving the charged particles 73 adjacent to the porous diffusion layer 77, thereby limiting passage of the active molecules 78 and 79. As shown in FIG. 7A, different microcells include different active molecules 78 and 79. With the application of a voltage of a suitable polarity and magnitude, the particles 75 are pushed to the "bottom" of the delivery system. If desired, the polarity could be flipped, thereby driving the charged particles 73 away from the porous diffusion layer 77. In some embodiments, it will not be necessary to provide an electrode 75 on both sides of the mixture containing the active molecules 78 and 79 and the charged particles 73. For instance, as shown in FIG. 7B a voltage source may be grounded into the surface to which the delivery system is attached. This may be especially useful for transdermal delivery of drugs, where the skin's natural conductance is sufficient to provide a ground potential. Thus in FIG. 7B the charged particles 73 are moved adjacent to the porous diffusion layer 77 with application of a potential to an electrode 75 above the mixture. It is appreciated that the top electrode 75 may not be a continuous electrode, but rather an active matrix of electrodes whereby individual "pixel" electrodes can be addressed, e.g., with row-column drivers as in an electro-optic display. FIG. 7B additionally illustrates that different microcells can be filled with mixtures including different concentrations of active molecules 78.

FIG. 7C illustrates an alternative embodiment whereby magnetic particles 74 are driven adjacent the porous diffusion layer 77 with a magnetic field. As shown in FIG. 7C, the magnetic particles 74 that are in the strongest magnetic field will move, while other magnetic particles 74 maintain their position away from the porous diffusion layer 77. While FIG. 7C depicts a singular external magnet, it is understood that an array of electromagnets situated over the microcell array could be used to address particular microcells on demand. As shown in FIG. 7C, some microcells contain a first active molecule 78, while other microcells contain a second active molecule 79. Other embodiments (not shown) may include a combination of both magnetic 74 and charged 73 particles.

Figure 8:
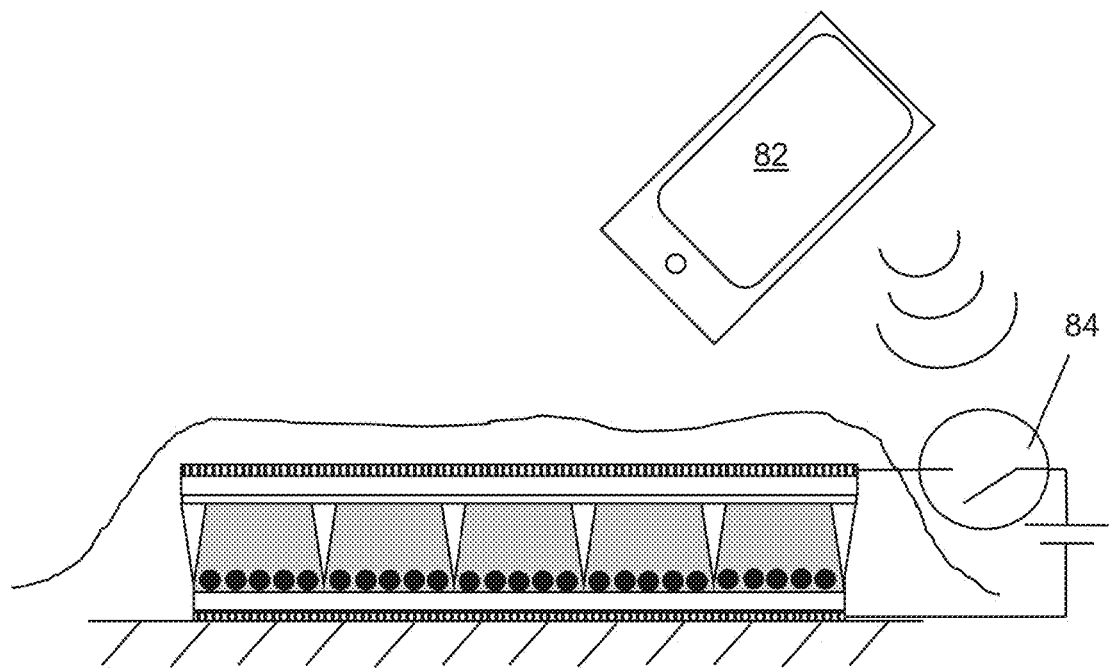
FIG. 8 illustrates an embodiment of an active molecule delivery system including a plurality of microcells and charged particles to regulate motion of active ingredients across a porous diffusion layer.
Figure 9:
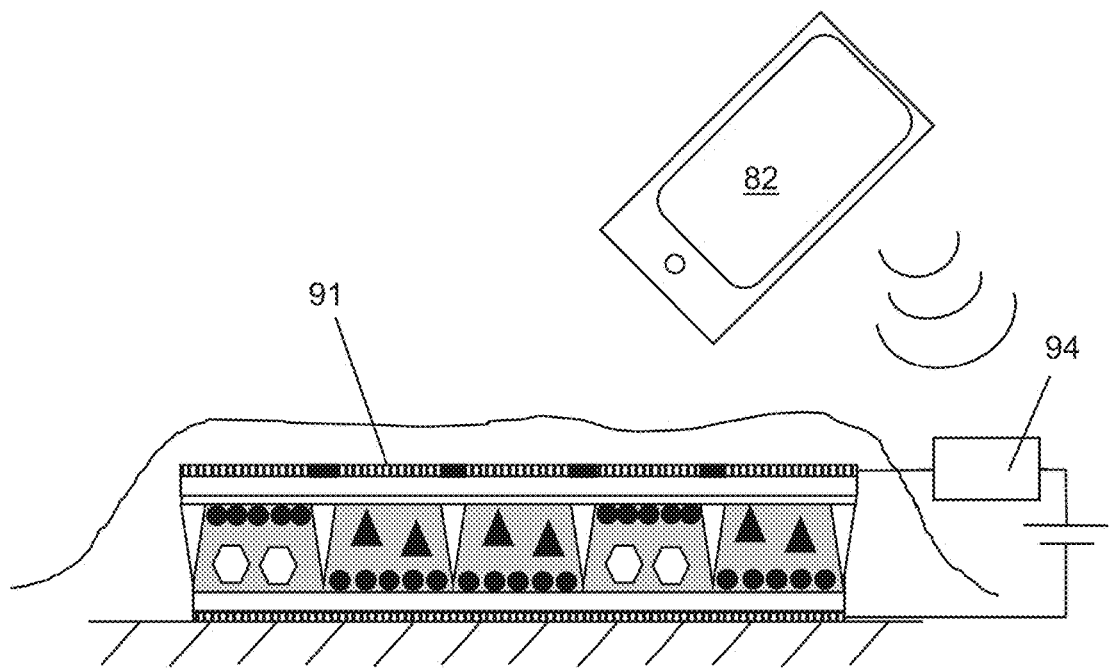
FIG. 9 illustrates an embodiment of an active molecule delivery system including a plurality of microcells and charged particles to regulate motion of active ingredients across a porous diffusion layer.

Advanced embodiments of an active molecule delivery system will include circuitry to allow the active molecule delivery system to be controlled wirelessly with a secondary device 82, such as a smart phone or smart watch. As shown in FIG. 8, a simple system will allow a user to open an electronic/digital switch 84 which will cause an electric field to be delivered to electrodes, thereby driving charged particles away from the porous diffusion layer and giving the user a dose of the active molecules. In advanced embodiments, i.e., as shown in FIG. 9, the active molecule delivery system will include an active matrix of electrodes 91 that are controlled by a controller 94, which is also able to receive wireless signals from a secondary device 82. The embodiment of FIG. 9 will allow a user to control, for example, the type of active molecule that is delivered and the amount. Using an application on the secondary device 82 it may be possible to program the active molecule delivery system to modify the amount of active molecule delivered based upon the time of day. In other embodiments, the application may be operatively connected to biometric sensors, e.g., a fitness tracker, whereby the application causes the dosage to be turned off if, e.g., the pulse rate of the user exceeds a preset threshold.

When driving the patches of FIGS. 8 and 9, NFC, Bluetooth, WIFI, or other wireless communication function is turned on allowing a user to manipulate the charged or magnetic particles in the microcells to move them to different positon electrophoretically or magnetically. The patch driving can be done before or after the patch is applied on skin surface and drug release adjustment can be achieved at any time when necessary by re-driving the patch due to the battery-free feature. When the charged or magnetic particles are driven to different positions, the releasing profiles will be altered due to interaction with the porous diffusion layer. Because the driving is controlled by smart watch or smart phone, the percentage and area for all of the microcells at different driving status is known, which means all of the usage data will be available to a provider or therapist, including when the patch is activated and what amount of active is administered. For the "on demand" function, whenever the patient or the doctor feel the necessity to adjust the drug releasing, the patch can be re-driven. For the "programmable" feature, because every microcell can be turned independently, the overall releasing of patch can be programmed by driving the charged particles to different level at various segments. Because the patch after driving is segmented, the skin irritation can also be controlled. Additionally, patient compliance is also good because the smart device that is used to activate the patch can also communicate with doctors remotely for data sharing.

Figure 10A:
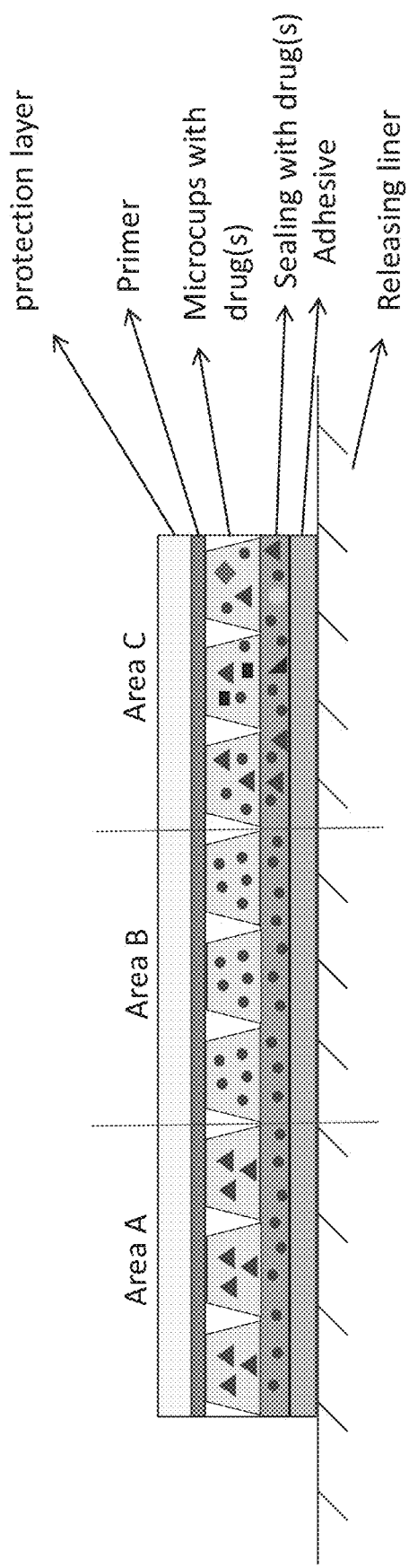
FIGS. 10A and 10B illustrate delivery of actives by loading the actives in additional layers of the active molecule delivery system. Different combinations of actives can be included in different areas of the delivery system.
Figure 10B:
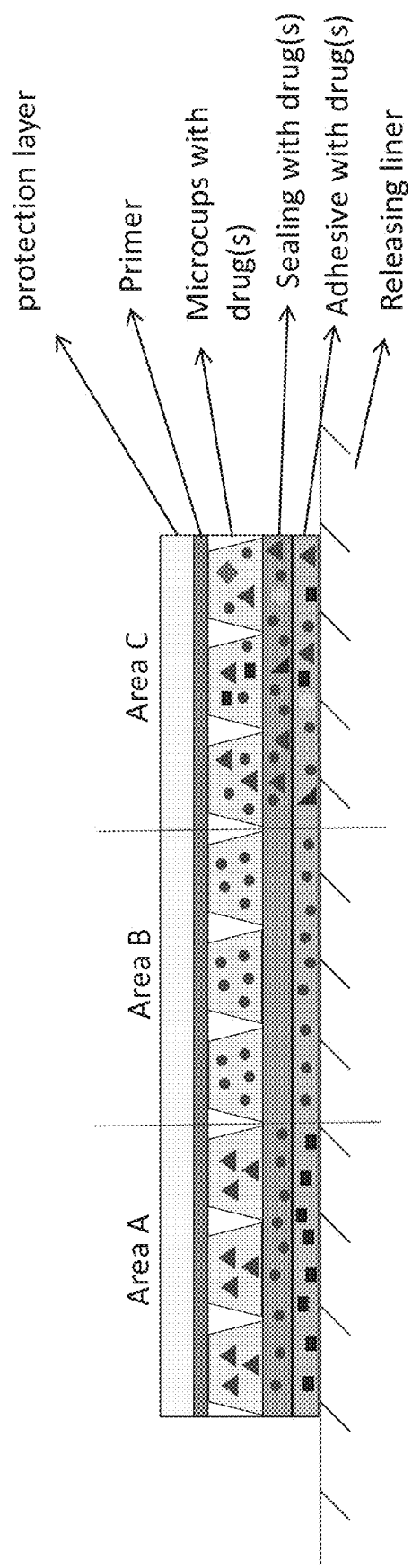

It is to be understood that the invention is not limited to combinations of actives in the microcell, as different actives can be delivered by adding those actives to additional layers of the drug delivery system. As shown in FIGS. 10A and 10B, the actives may be present in, for example, the sealing layer, adhesive layer, or an additional drug release layer.

Area A of FIGS. 10A and 10B exemplifies two different actives (e.g., drugs) being loaded into the microcell layer and the sealing layer, respectively. In some embodiments, the two drugs may be delivered at the same time, however they may also have different delivery profiles. The system also provides a way to deliver different actives with different hydrophobicities. For example, if the formulation within the microcell is water-based, a hydrophilic active can be loaded into microcell at high loading. In this embodiment, the sealing layer will include a hydrophobic material which is suitable to load a hydrophobic active. Accordingly, the release profile of the two drugs can also be adjusted nearly independently. This system overcomes the problem of stabilizing an active with unfavorable solubility with, e.g., surfactants, capsules, etc.

Area B of FIGS. 10A and 10B illustrates an embodiment in which the same drug is loaded in both internal phase and sealing layer. Depending on drug characteristics, this method can help to load larger quantities of drug into the drug release device, which can help to increase drug release amount and adjust releasing profile.

Area C of FIGS. 10A and 10B illustrates an embodiment in which a combination of actives is loaded into either the microcell, or the sealing layer, or both layers. Again, the actives(s) in the microcell formulation and sealing layer can be the same or different. The number of actives in the microcell formulation and the number of actives in the sealing layer can also be the same or different.

As shown in FIG. 10B, the adhesive layer can also be loaded with active(s). The amount and types of actives in the adhesive layer can be independent of the loading in sealing layer and/or the microcell formulation. The active can be introduced into only some portions of the adhesive layer, or it can present in both adhesive and sealing layer (see, e.g., Area A of FIG. 10B).

Example—Controlling Nicotine Release with Blocking Particles

Figure 11:
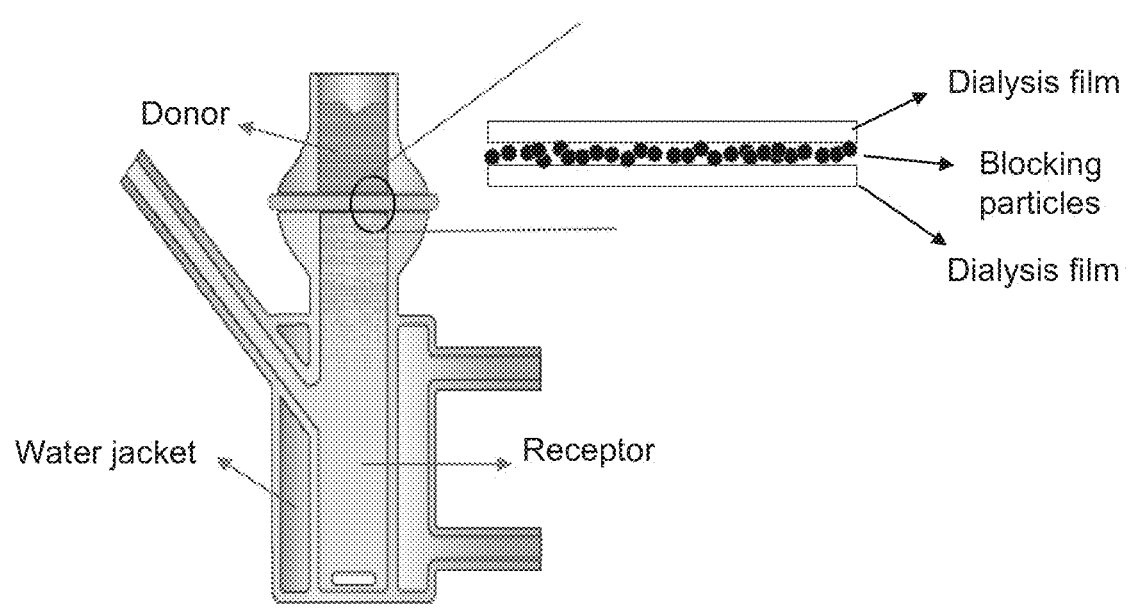
FIG. 11 illustrates the use of a Franz cell for measuring rates of diffusion through a porous layer both with and without blocking particles.

FIG. 11 shows a Franz cell apparatus that was used to demonstrate that a dosing profile can be altered with particles sufficient to obstruct the pores of a diffusion membrane. In brief, a Pyrex Franz cell (PermeGear, Inc., Hellertown, Pa.) was obtained and assembled as shown in FIG. 11. Two layers of dialysis tubing (Thermo-Fisher, Waltham, Mass.) were cut to fit across the opening at the joint of the Franz cell. For control measurements, 500 μL of a 1.3 mg/mL solution of nicotine in D.I. water was pipetted into the top of the cell. Samples were removed from the receptor cell at various time points as indicated in the graph in FIG. 12. The samples were later analyzed to determine the total amount of nicotine that had passed the double layer barrier, thereby resulting in the data points represented by the squares.

Subsequent experiments added small amounts of polymer-coated carbon nanoparticles between the two layers of dialysis tubing. The overall coverage was approximated by taking a photograph of the combined double layer nanoparticle sandwich from the top and assessing the darkness of the layer. Darker sandwiched layers corresponded to greater coverage. For approximately 35% coverage [circles] and for full (100%) coverage [triangles], a sample of 500 µL of a 1.3 mg/mL solution of nicotine in D.I. water was pipetted into the top of the cell and samples were removed at various time points.

Figure 12:
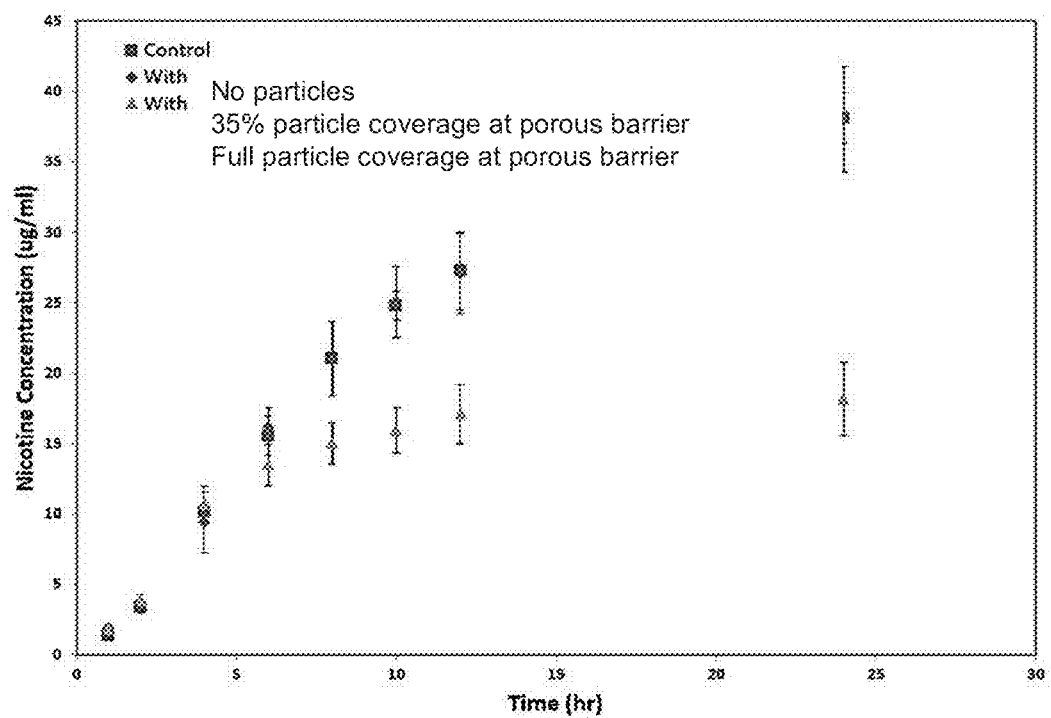
FIG. 12 shows nicotine release profiles through a porous diffusion layer when particles are used to regulate the rate of nicotine movement through a porous diffusion layer.

As can be seen in FIG. 12, the 35% coverage release profile was very similar to the control, suggesting that the rate of diffusion through the non-covered areas may have been so much greater than the covered areas that the effect of 35% coverage was negligible. However, the fully-covered sandwich of dialysis tubing and carbon nanoparticles showed a sizeable difference in the release profile as well as a 50% reduction in the total nicotine delivered over 24 hours. This test suggests that charged or magnetic particles paired with a suitable porous layer will allow on-demand reduction in dosing.

Thus the invention provides for an active molecule delivery system including a plurality of microcells. The microcells include active molecules, e.g., drugs, as well as charged or magnetic particles. The microcells include an opening that is spanned by a porous diffusion layer. Because the microcells include charged or magnetic particles that are suitably sized to block the porous diffusion layer, it is possible to regulate the delivery of the active molecules with the application of an electric or magnetic field. This disclosure is not limiting, and other modifications to the invention, not described, but self-evident to one of skill in the art, are to be included in the scope of the invention.

The invention claimed is:

1. An active molecule delivery system comprising:
a plurality of microcells, wherein each microcell includes an opening and a mixture of an active molecule and magnetic particles, wherein the magnetic particles are associated with steric-stabilizing molecules selected from the group consisting of polyethylene, polypropylene, polyester, polysiloxane and mixtures thereof;
a porous diffusion layer spanning the opening of each microcell; and
a source of a magnetic field.

2. The active molecule delivery system of claim 1, further comprising an adhesive layer adjacent the porous diffusion layer.

3. The active molecule delivery system of claim 1, wherein the microcell includes a mixture of an active molecule and magnetic particles, and wherein the magnetic particles are movable within the microcell with the source of a magnetic field.

4. The active molecule delivery system of claim 3, wherein the magnetic particles limit diffusion of the active molecule across the porous diffusion layer when the magnetic particles are adjacent to the porous diffusion layer.

5. The active molecule delivery system of claim 3, wherein the source of a magnetic field is an electromagnet.

6. The active molecule delivery system of claim 5, wherein the electromagnet is a part of a matrix of electromagnets, wherein individual electromagnets in the matrix are addressable.

7. The active molecule delivery system of claim 1, wherein the porous diffusion layer comprises an acrylate, a methacrylate, a polycarbonate, a polyvinyl alcohol, cellulose, poly(N-isopropylacrylamide) (PNIPAAm), poly(lactic-co-glycolic acid) (PLGA), polyvinylidene chloride, acrylonitrile, amorphous nylon, oriented polyester, terephthalate, polyvinyl chloride, polyethylene, polypropylene, or polystyrene.

8. The active molecule delivery system of claim 1, wherein the mixture of an active molecule and magnetic particles is distributed in a biocompatible non-polar liquid.

9. The active molecule delivery system of claim 8, wherein the biocompatible non-polar liquid is vegetable, fruit, or nut oil.

10. The active molecule delivery system of claim 1, the mixture of an active molecule and magnetic particles is distributed in an aqueous liquid.

11. The active molecule delivery system of claim 1, wherein the active molecule is a pharmaceutical compound.

12. The active molecule delivery system of claim 1, wherein the plurality of microcells comprises first microcells containing a mixture of first active molecules and second microcells containing a mixture of second active molecules.

13. The active molecule delivery system of claim 1, wherein the plurality of microcells comprises first microcells containing active molecules at a first concentration and second microcells containing active molecules at a second concentration.

14. The active molecule delivery system of claim 1, wherein the plurality of microcells comprises first microcells containing a mixture of active molecules and second microcells containing an adjuvant.

15. The active molecule delivery system of claim 1, wherein each of the plurality of microcells has a volume greater than 100 nL.

16. The active molecule delivery system of claim 1, wherein the porous diffusion layer has an average pore size of between 10 nm and 100 µm.

* * * * *